United States Patent [19]
Hayashizaki et al.

[11] Patent Number: 6,093,300
[45] Date of Patent: *Jul. 25, 2000

[54] SAMPLE PLATE AND MULTI-CAPILLARY ELECTROPHORESIS APPARATUS

[75] Inventors: Yoshihide Hayashizaki, Ibaraki; Shin Nakamura, Kyoto, both of Japan

[73] Assignees: Japan Science and Technology Corporation, Kawaguchi; The Institute of Physical and Chemical Research, Wako; Shimadzu Corporation, Kyoto, all of Japan

[ * ] Notice: This patent issued on a continued prosecution application filed under 37 CFR 1.53(d), and is subject to the twenty year patent term provisions of 35 U.S.C. 154(a)(2).

[21] Appl. No.: 09/037,005

[22] Filed: Mar. 9, 1998

[30] Foreign Application Priority Data

Mar. 10, 1997 [JP] Japan ..................................... 9-074395
Mar. 10, 1997 [JP] Japan ..................................... 9-074396

[51] Int. Cl.$^7$ .......................... G01N 27/26; G01N 27/447
[52] U.S. Cl. .......................... 204/604; 204/451; 204/453; 204/601; 422/100; 436/809
[58] Field of Search ..................................... 204/601, 602, 204/603, 604, 605, 451, 452, 453, 454, 455; 422/102, 104, 58; 436/809

[56] References Cited

U.S. PATENT DOCUMENTS

| | | | |
|---|---|---|---|
| 4,302,533 | 11/1981 | Revel et al. ................................. | 435/4 |
| 4,735,778 | 4/1988 | Maruyama et al. ...................... | 422/102 |
| 5,560,811 | 10/1996 | Briggs et al. .............................. | 204/451 |
| 5,567,294 | 10/1996 | Dovichi et al. .......................... | 204/603 |
| 5,605,662 | 2/1997 | Heller et al. ......................... | 204/601 X |
| 5,730,850 | 3/1998 | Kambara et al. ........................ | 204/603 |

FOREIGN PATENT DOCUMENTS

| | | |
|---|---|---|
| 0 723 149 | 7/1996 | European Pat. Off. . |
| 8-233778 | 9/1996 | Japan . |
| 93 17325 | 9/1993 | WIPO . |
| 94 29712 | 12/1994 | WIPO . |

OTHER PUBLICATIONS

Marten Jansson et al., "Micro vials on a silicon wafer for sample introduction in capillary electrophoresis" Journal of Chromatography, vol. 626 (1992) 310–314.

*Primary Examiner*—Jill Warden
*Assistant Examiner*—John S. Starsiak, Jr.
*Attorney, Agent, or Firm*—Armstrong, Westerman, Hattori, McLeland & Naughton

[57] ABSTRACT

A base plate is made of an insulating material, and comprised of a flat surface and a connector part connected therewith. A plurality of wells are vertically and transversely arranged on the surface of the base plate at regular intervals respectively, and the respective wells are provided with individual electrode patterns reaching the connector part from bottoms thereof through the surface of the base plate. The connector part is connected to an external high-voltage application part.

6 Claims, 4 Drawing Sheets

SAMPLE PLATE AND MULTI-CAPILLARY ELECTROPHORESIS APPARATUS

BACKGROUND OF THE INVENTION

1. Field of the Invention

The present invention relates to a multi-capillary electrophoresis apparatus comprised of a plurality of capillary columns, and a sample plate employed for introducing samples into the plurality of capillary columns. The multi-capillary electrophoresis apparatus is comprised of a multi-capillary array migration part provided with a plurality of capillary columns for injecting a plurality of samples one by one into the capillary columns and electrophoresing the samples, and an optical measuring part for irradiating the capillary columns with light and measuring absorbance by or fluorescence from the samples in the irradiated parts.

2. Description of the Prior Art

In general, the multi-capillary electrophoresis apparatus is employed for separating proteins or determining the base sequence of DNA. The multi-capillary electrophoresis apparatus for determining the base sequence of DNA is used for electrophoresing a DNA fragment sample prepared by labeling a primer or a terminator with a fluorescent material using Sanger's reaction and detecting fluorescence from the DNA fragment sample during migration, thereby determining the base sequence.

A DNA sequencer with high sensitivity, a high speed and high throughput is necessary for determining the base sequences of DNA such as human genomes, which have long base sequences. Accordingly, a multi-capillary DNA sequencer that has a plurality of capillary columns charged with gels has been proposed in place of those employing flat plate type slab gels. In comparison with the slab gels, the capillary columns can readily handle, inject and electrophorese samples at a high speed and make highly sensitive detections. If a high voltage is applied in slab gels, bands are spread due to the influence of Joulean heat, or temperature gradients are caused. Conversely, capillary columns have no such problems, but make highly sensitive detections with minimal spreading of bands under high-speed electrophoresis with the application of a high voltage.

In such capillary electrophoresis, samples are introduced into the capillary columns by a method employing pressure or an electrophoretic method applying a voltage. The method of electrophoretically introducing samples is widely employed because of simplicity in apparatus structure, readiness in operation and excellent controllability of parameters.

In the case of electrophoretically introducing samples, it is necessary to dip first and second end portions of the capillary columns in prepared samples and a buffer solution respectively while dipping electrodes such as platinum wires in the samples in the vicinity of capillary column ends.

In the case of holding the electrodes in the vicinity of the end portions of the capillary columns in electrophoretic sample introduction, electrode structures are complicated in the use of a multi-capillary electrophoresis apparatus, which arranges a plurality of capillary columns together in the form of an array and simultaneously electrophoreses samples.

After the samples are injected into the capillary columns by a method of applying a voltage, the capillary column ends must be transferred to a reservoir which stores a buffer solution for migration, and hence it takes a long time after sample injection for migration to begin. Therefore, automatization can speed up this process.

SUMMARY OF THE INVENTION

The first object of the present invention is to provide a sample plate for sample introduction which has a simple electrode structure suitable for a multi-capillary electrophoresis apparatus.

The second object of the present invention is to provide a multi-capillary electrophoresis apparatus which can automatize operations from sample injection into a number of capillary columns up to migration with such a sample plate.

The sample plate according to the present invention is comprises of a base plate which is made of insulating resin, and has a plurality of bottomed holes formed as wells arranged two-dimensionally on a flat surface, electrodes positioned on the bottom portions of the respective wells, and a connector part for connecting these electrodes to an external power supply circuit The electrodes of the respective wells are electrically independent of or electrically connected to each other. When the electrodes of the respective wells are electrically independent of each other, individual voltages or the same voltage can be applied thereto. If the electrodes of the respective wells are electrically connected to each other, the same voltage is simultaneously applied to all electrodes.

According to one aspect of the present invention, in which the electrodes of the respective wells are electrically independent of each other, the connector part is connected with the surface of the base plate, and the electrodes of the wells are connected with the connector part by electrode patterns reaching the connector part through the base plate surface.

In regards to another aspect of the present invention, in which the electrodes of the respective wells are electrically connected to each other, the base plate is of such a throwaway type that the bottom portions of the wells are set at a thickness allowing the formation of through holes with metal projections. The sample plate is further comprised of an electrode plate of a conductive metal which has projections on positions corresponding to the wells of the base plate on its flat surface for serving as the electrodes and a connector part, and a fixing member for fixing the plates to each other while inserting the projections of the electrode plate into the wells from the rear side of the base plate.

The multi-capillary electrophoresis apparatus of the present invention is comprised of a multi-capillary array migration part which has a plurality of capillary columns for injecting a plurality of samples one by one into the capillary columns and simultaneously electrophoresing the samples in all capillary columns, and an optical measuring part for irradiating the capillary columns with light and measuring the absorbance of the light or fluorescence from the samples in the irradiated parts. Capillary column ends are two-dimensionally arranged downward on a sample injection side of the multi-capillary array migration part The sample plate provided with two-dimensionally arranged wells storing samples in correspondence with the arrangement of the capillary column ends, and a first migration reservoir storing a buffer solution for applying a voltage to all capillary columns are arranged under the capillary column ends. The aforementioned sample plate of the present invention forms this sample plate. A moving mechanism is provided for bringing either the sample plate or the first migration reservoir into contact with the capillary column ends switching them.

During sample injection into the capillary columns, samples are introduced into the sample plate's wells respectively, and the moving mechanism moves the sample plate for dipping the first ends of the respective capillary columns into the samples introduced into the wells. A voltage is applied between the connector part of the sample plate and a buffer solution stored in a second migration reservoir, receiving the second ends of the capillary columns for electrophoretically introducing the samples into the capillary columns. After the sample injection, the moving mechanism separates the sample plate from the first ends of the capillary columns, and dips these first ends into the buffer solution stored in the migration reservoir. Thereafter, a voltage is applied between the buffer solutions in the first and second migration reservoirs provided on both ends of the capillary columns for migrating the samples. Thus, operations from sample injection into the capillary columns up to migration are automatically performed.

While already treated samples may be introduced into the wells of the sample plate, samples may also be treated by a PCR (polymerase chain reaction) method through the wells of the sample plate, after which the capillary ends are inserted in the treated samples stored in the wells for sample injection. The PCR method is a method of remarkably amplifying only a specific part of DNA. This PCR method can be adapted to apply a primer to a sample DNA; dissociate double-stranded DNA to single-stranded DNA by increasing the temperature, then couple the primer to the single-stranded DNA chains by reducing the temperature; synthesize DNA by slightly increasing the temperature and again make single-stranded DNA by further increasing the temperature. The PCR method amplifies/synthesizes prescribed parts of DNA by repeating the operation of increasing and reducing the temperature.

The sample plate of the present invention is comprised of the base plate which has two-dimensionally arranged bottomed wells on the flat surface, the electrodes positioned on the bottom portions of the respective wells, and the connector part connecting the electrodes with the external power supply circuit. When this sample plate is employed, therefore, the electrodes can be wired on a plurality of wells without a complicated electrode wiring structure. In particular, samples can be readily injected into the capillary columns in the electrophoresis apparatus employing the multi-capillary array with a number of capillary columns.

The multi-capillary electrophoresis apparatus of according to the present invention employs this sample plate for sample injection and comprises the moving mechanism for bringing either the sample plate or the migration reservoir into contact with the capillary column ends, whereby sample injection into the capillary columns and migration can be automatically performed.

The foregoing and other objects, features, aspects and advantages of the present invention will become more apparent from the following detailed description of the present invention when considered in conjunction with the accompanying drawings.

DESCRIPTION OF THE PREFERRED EMBODIMENTS

Figure 1A:
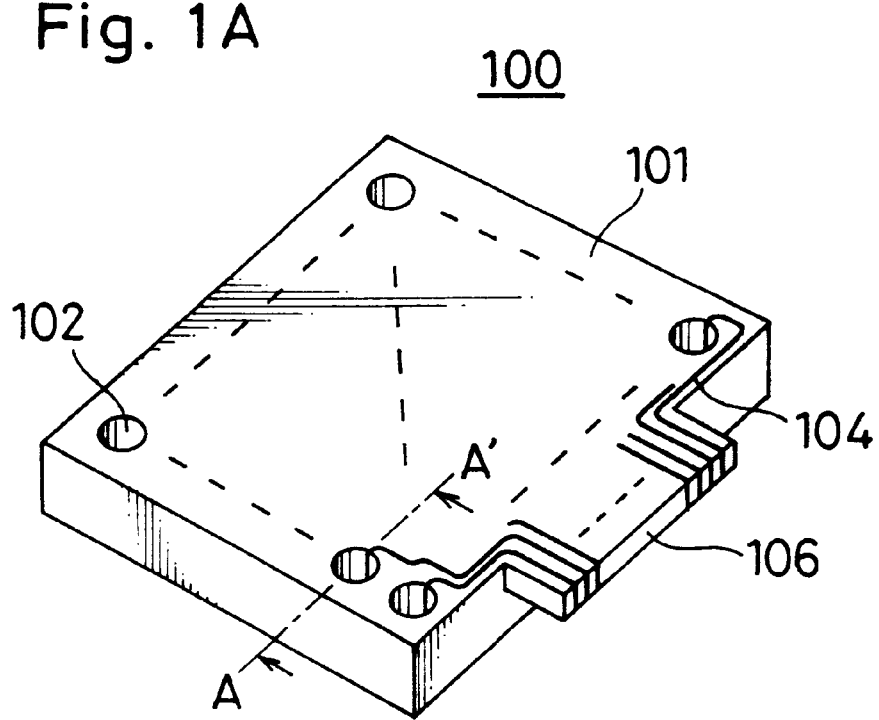
FIG. 1A is a schematic perspective view showing a sample plate according to an embodiment of the present invention.
Figure 1B:
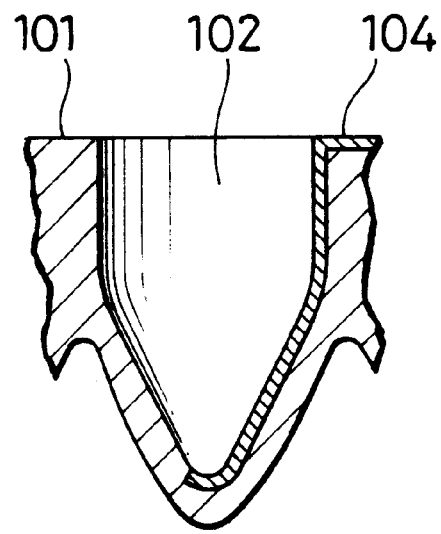
FIG. 1B is a sectional view taken along the line A–A' in FIG. 1A.

FIG. 1A is a schematic perspective view showing sample plate 100 according to an embodiment of the present invention, and FIG. 1B is a sectional view taken along the line A–A' in FIG. 1A, illustrating the sectional structure of a single well.

Base plate 101 of sample plate 100 is made of an insulating material, and is comprised of a flat surface and connector part 106 connected therewith. The material for base plate 101 is properly prepared from heat-resistant engineering plastic such as polyether sulfone, polyether imide, polysulfone or liquid crystal polymer. A plurality of wells 102 are vertically and transversely arranged on the surface of base plate 101 at regular intervals. Wells 102, which are bottomed holes, are provided with individual electrode patterns 104 reaching connector part 106 from the bottoms thereof through the surface of base plate 101. Connector part 106 is connected to an external high-voltage application part.

Electrode patterns 104 are formed as three-dimensional wiring patterns reaching connector part 106 from the bottoms of wells 102 through the internal wall surfaces of wells 102 and the surface of base plate 101. Such wiring patterns can be formed by utilizing an MID (molded interconnect device) fabricating method of forming conductive wiring patterns on a resin molding, by forming base plate 101 by a molding method and thereafter by plating a conductive material such as copper or nickel on the molding by electroless plating. In concern of adsorption of samples and influence exerted by metal ions on the samples, gold plating is preferable on electrode patterns 104.

Electrode patterns 104 are individually provided in wells 102 and guided to connector part 106, whereby different voltages can be applied to electrodes of wells 102 or the same voltage can be simultaneously applied to all or some wells 102.

Figure 2A:
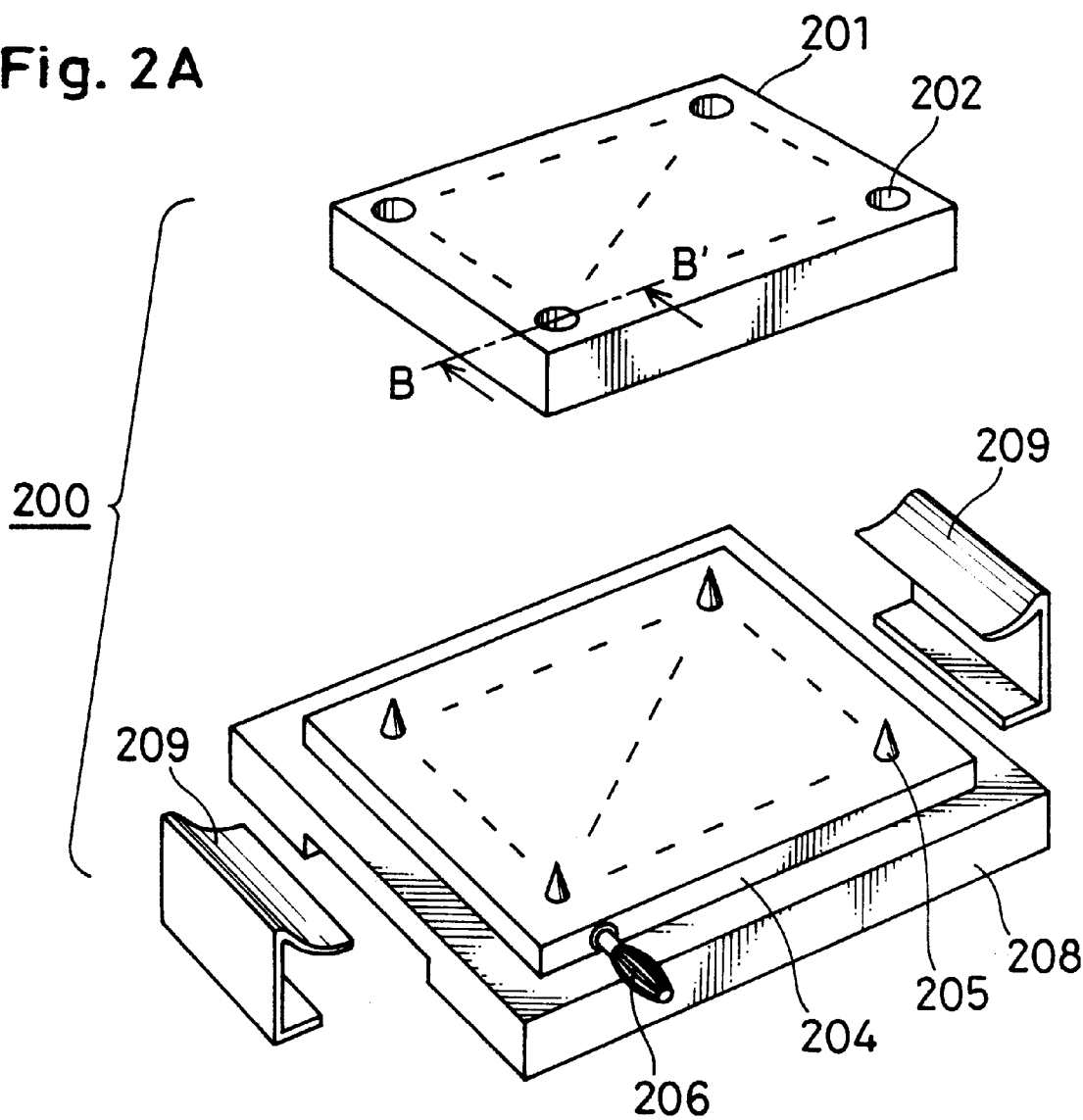
FIG. 2A is a schematic perspective view showing a sample plate according to another embodiment of the present invention.
Figure 2B:
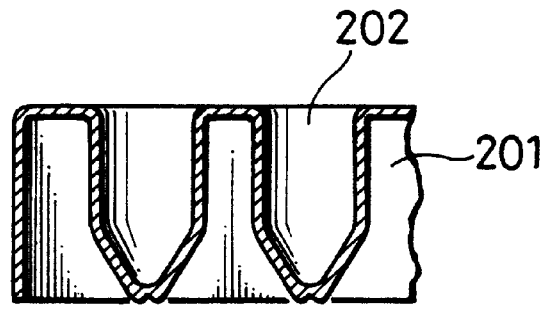
FIG. 2B is a sectional view taken along the line B–B' in FIG. 2A.

FIG. 2A illustrates sample plate 200 according to another embodiment of the present invention. FIG. 2B is a sectional view taken along the line B–B' in FIG. 2A.

A commercially available micro titer plate may be adapted to form base plate 201. Base plate 201 is formed by thin plastic as a whole, and wells 202 of bottomed holes are vertically and transversely arranged on its flat surface at regular intervals. Base plate 201 is made of soft molding resin such as polypropylene or polyethylene. Through holes can be readily formed on the bottom portions of wells 202 by inserting metal projections.

Electrode plate 204, which is made of a conductive material such as stainless steel having high mechanical strength, is provided with projections 205 vertically and transversely arranged at regular intervals on its flat surface in correspondence to wells 202 of base plate 201. Projections 205, which are inserted into wells 202 from the bottom portions thereof to be in contact with samples, are preferably coated with gold plating layers in consideration of adsorption of the samples and influence exerted by metal ions on the samples. Plug 206, which serves as a part to be connected to a high-voltage power source, is provided on a side of electrode plate 204.

Electrode plate 204 is fixed to insulating holder 208. Clamps 209 are provided between holder 208 and base plate 201 for bringing base plate 201 and electrode plate 204 into close contact with each other in a pressurized state while penetrating the bottom portions of wells 202 with projections 205 and superimposing base plate 201 on electrode plate 204. Clamps 209 may be replaced with cap screws or other means of applying pressure.

When samples are introduced into wells 202 and projections 205 of electrode plate 204 are inserted into the bottom portions of wells 202, the bottom portions of wells 202 seal projections 205 since base plate 201 is made of soft molding resin to prevent leakage of the samples in wells 202.

After use, electrode plate 204 is detached from the plate 201. While base plate 201 is discarded after a single use, electrode plate 204 is used repetitively. Electrode plate 204 must be cleaned for reuse. In particular, projections 205 to be brought into contact with samples must be carefully cleaned for reuse.

In sample plate 200 shown in FIG. 2A, projections 205 are formed on common electrode plate 204 and electrically connected to each other so that the same voltage is applied to all projections 205 for serving as electrodes. When electrode plate 204 is made of an insulating material and provided with plugs corresponding to conductive projections 205, however, individual voltages can be applied to respective wells 202.

Figure 3:
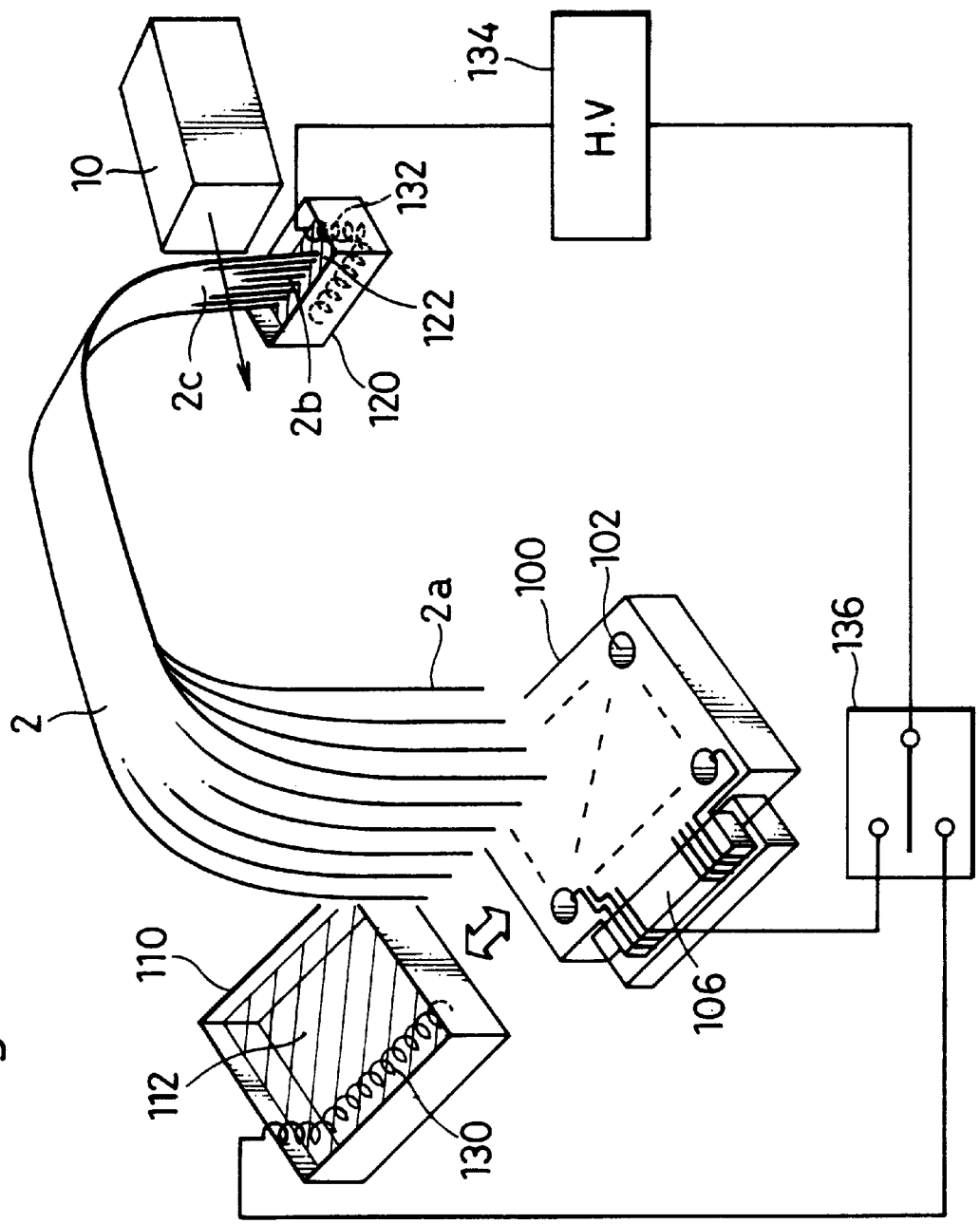
FIG. 3 is a schematic perspective view showing a multi-capillary electrophoresis apparatus according to an embodiment of the present invention for injecting samples with the sample plate shown in FIG. 1A.

FIG. 3 schematically illustrates a multi-capillary electrophoresis apparatus employing sample plate 100 shown in FIG. 1A for sample injection.

While general multi-capillary electrophoresis apparatuses include a gel electrophoresis apparatus having capillary columns charged with gels such as polyacrylic amide gels, linear acrylic amide gels or polyethylene oxide (PEO) gels as separation media, and a capillary zone electrophoresis apparatus making free migration in capillary columns with no gels; sample plate 100 according to the present invention is applicable to any electrophoresis apparatus as long as it employs a plurality of capillary columns.

A pair of reservoirs 110 and 120 are filled with buffer solutions 112 and 122 respectively, and electrodes 130 and 132 are provided in buffer solutions 112 and 122 respectively. Samples are introduced into respective wells 102 of sample plate 100 shown in FIG. 1A, and a high-voltage wiring cable is connected to connector part 106.

High-voltage switching part 136 connects reservoir 110 and sample plate 100 making the unit capable of being switched; and electrophoretic high-voltage power source 134 is connected between high-voltage switching part 136 and electrodes 132 provided in the other reservoir 120, for applying a sample injection voltage and a migration voltage.

In sample injection, first end portions 2a of capillary columns forming capillary array 2 are inserted one by one into wells 102 of sample plate 100. After the samples are injected, first end portions 2a are dipped in buffer solution 112 stored in reservoir 110. Second end portions 2b of the capillary columns forming capillary array 2 are dipped in buffer solution 122 stored in the other reservoir 120. These second end portions 2b are provided with detecting parts 2c irradiated with measuring light or excitation light from optical measuring part 10 for detecting the samples by absorbance or fluorescence.

The capillary columns forming capillary array 2 are two-dimensionally arranged on first end portions 2a in correspondence to the arrangement of wells 102 in sample plate 100, and aligned with each other on detecting parts 2c to be irradiated with the measuring light or excitation light from a direction perpendicular to the arranged plane thereof.

A moving mechanism (not shown) switches sample plate 100 and reservoir 110 as indicated by the broad arrow in FIG. 3 so that either one of these selectively comes into contact with first end portions 2a of the capillary columns. The moving mechanism moves sample plate 100 and reservoir 110 in a horizontal plane, and also perpendicularly moves the same for bringing sample plate 100 or reservoir 110 into contact with first end portions 2a of the capillary columns.

In sample injection, first end portions 2a of the capillary columns are dipped one by one into the samples in wells 102 of sample plate 100, while second end portions 2b of the capillary columns are dipped together in buffer solution 122 stored in reservoir 120. A high voltage is simultaneously or successively applied to all wells 102 through electrode patterns 104 for injecting the samples into the capillary columns. A switching part may be provided for successively applying the high voltage to wells 102. When a plurality of high-voltage application means are prepared, the samples can be introduced under different introduction conditions.

After the sample injection, the application of the high voltage is temporarily stopped and the moving mechanism moves sample plate 100 and reservoir 110 for dipping first end portions 2a of the capillary columns in buffer solution 112 stored in reservoir 110. Thereafter a high voltage is applied between reservoirs 110 and 120 for performing electrophoretic separation. The sample injection voltage and a power supply voltage for migration may be set at 30 kV, for example, and a current capacity is 10 to 30 mA.

The moving mechanism may move sample plate 100 and reservoir 110 in the horizontal plane while perpendicularly moving first end portions 2a of the capillary columns.

The number of wells 102 of sample plate 110 can be arbitrarily set in response to the number of the capillary columns.

Reservoir 110 may be provided with a plurality of wells filled with buffer solution 112 similarly to sample plate 100, and the respective wells may be provided with individual electrode patterns so that independent voltages can be applied to the wells for simultaneously making electrophoresis under different conditions.

Figure 4:
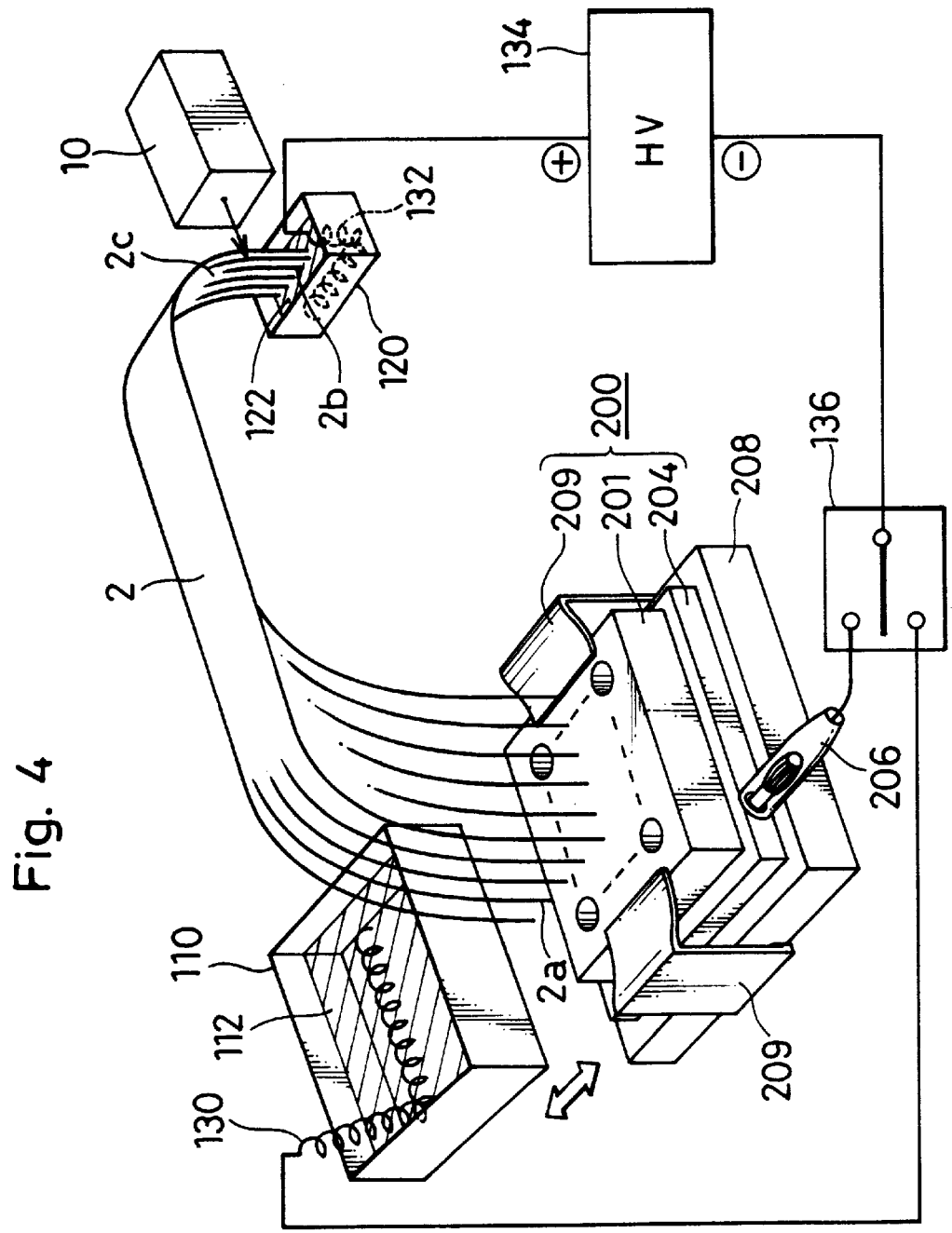
FIG. 4 is a schematic perspective view showing a multi-capillary electrophoresis apparatus according to another embodiment of the present invention for injecting samples with the sample plate shown in FIG. 2A.

FIG. 4 schematically illustrates a multi-capillary electrophoresis apparatus employing sample plate 200 (shown in FIG. 2A) for sample injection.

The structure of this multi-capillary electrophoresis apparatus is identical to that shown in FIG. 3 except for sample plate 200, and hence redundant description is omitted.

A pair of reservoirs 110 and 120 are filled with buffer solutions 112 and 122 respectively, and electrodes 130 and 132 are provided in buffer solutions 112 and 122 respectively. Samples are introduced into respective wells 202 of base plate 201 of sample plate 200, projections 205 of electrode plate 204 are inserted into the bottom portions of wells 202 to be brought into contact with the samples, and clamps 209 closely fix plates 201 and 204 to each other. A high-voltage wiring cable is connected to plug 206.

High-voltage switching part 136 connects reservoir 110 and sample plate 200 making the unit capable of switching wires, and an electrophoretic high-voltage power source 134 is connected between high-voltage switching part 136 and electrode 132 in reservoir 120 for applying a sample injection voltage and a migration voltage.

In sample injection, first end portions 2a of capillary columns are inserted one by one into wells 202 of sample plate 200. After the samples are injected, first end portions 2a are dipped into buffer solution 112 stored in reservoir 110.

A moving mechanism (not shown) switches sample plate 200 and reservoir 110 as indicated by the broad arrow in FIG. 4 so that either one of these selectively comes into contact with first end portions 2a of the capillary columns.

In sample injection, first end portions 2a of the capillary columns are dipped one by one into the samples in wells 202 of sample plate 200, while second end portions 2b of the capillary columns are dipped together in buffer solution 122 stored in reservoir 120. A high voltage is simultaneously applied to all wells 202 through projections 205 of electrode plate 204 for injecting the samples into the capillary columns.

Electrophoretic separation after the sample injection is identical to that described with reference to FIG. 3.

Although the present invention has been described and illustrated in detail, it is clearly understood that the same is by way of illustration and example only and is not to be taken by way of limitation, with the spirit and scope of the present invention being limited only by the terms of the appended claims.

What is claimed is:

1. A sample plate for introducing samples into capillary columns, comprising:

a base plate of insulating resin having a plurality of bottomed holes being formed as wells and two-dimensionally arranged on its flat surface;

electrodes being positioned on bottom portions of respective said wells; and a connector part for connecting said electrodes to an external power supply circuit, wherein said connector part is connected to said surface of said base plate, said electrodes of said wells are formed as electrode patterns, and said electrode patterns reach said connector part through said surface of said base plate to be connected to said connector part, and said electrodes of said respective wells are individual electrodes reaching said connector part, are electrically independent of each other, and are plated on said surface of said base plate.

2. The sample plate in accordance with claim 1, wherein said electrodes of respective said wells are formed as three-dimensional wiring patterns reaching said connector part.

3. A sample plate for introducing samples into capillary columns, comprising:

a base plate of insulating resin having a flat surface and a rear side opposed to said flat surface, and having a plurality of bottomed holes being formed as wells and two-dimensionally arranged on sail flat surface of said base plate;

electrodes being positioned on bottom portions of respective said wells; and a connector part for connecting said electrodes to an external power supply circuit, wherein said base plate is of such a throwaway type that said bottom portions of said wells are set at a thickness allowing formation of through holes with metal projections, said sample plate further comprising:

an electrode plate having a flat surface and having projections provided on said flat surface of said electrode plate in positions corresponding to said wells of said base plate for serving as said electrodes and having said connector part, and a fixing member for fixing said electrode plate and said base plate to each other while inserting said projections of said electrode plate into said wells from said rear side of said base plate.

4. A multi-capillary electrophoresis apparatus comprising a multi-capillary array migration part provided with a plurality of capillary columns for injecting a plurality of samples one by one into said capillary columns and simultaneously electrophoresing the samples in all said capillary columns, and an optical measuring part for irradiating said capillary columns with light in said multi capillary array migration part and measuring light absorption or luminescence by said samples in irradiated parts, wherein capillary column ends are two-dimensionally arranged downward on a sample injection side of said multi-capillary array migration part, and a sample plate provided with two-dimensionally arranged wells storing said samples in correspondence to the arrangement of said capillary column ends, and a migration reservoir storing a migration buffer solution for applying a voltage to all said capillary columns are arranged under said capillary column ends, said sample plate comprises a base plate of insulating resin having a plurality of bottomed holes being formed as wells and two-dimensionally arranged on its flat surface, electrodes positioned on bottom portions of respective said wells, and a connector part connecting said electrodes to an external power supply circuit, said sample plate and said migration reservoir are movable for bringing either one of these into contact with said capillary column ends, said connector part is connected to said surface of said base plate and said electrodes of respective said wells are connected to said connector part by electrode patterns reaching said connector part through said surface of said base plate in said sample plate, and said electrodes of said respective wells are individual electrodes reaching said connector part, are electrically independent of each other, and are plated on said surface of said base plate.

5. The multi-capillary electrophoresis apparatus in accordance with claim 4, wherein said electrodes of respective said wells are formed as three-dimensional wiring patterns reaching said connector part.

6. A multi-capillary electrophoresis apparatus comprising a multi-capillary array migration part provided with a plurality of capillary columns for injecting a plurality of samples one by one into said capillary columns and simultaneously electrophoresing the samples in all said capillary columns, and an optical measuring part for irradiating said capillary columns with light in said multi-capillary array migration part and measuring light absorption or luminescence by said samples in irradiated parts, wherein capillary column ends are two-dimensionally arranged downward on a sample injection side of said multi-capillary array migration part, and a sample plate provided with two-dimensionally arranged wells storing said samples in correspondence to the arrangement of said capillary column ends, and a migration reservoir storing a migration buffer solution for applying a voltage to all said capillary columns are arranged under said capillary column ends, said sample plate comprises a base plate of insulating resin having a flat surface and a rear side opposed to said flat surface and having a plurality of bottomed holes being formed as wells and two-dimensionally arranged on said flat surface of said sample plate, electrodes positioned on bottom portions of respective said wells, and a connector part connecting said electrodes to an external power supply circuit, and a moving mechanism is provided for switching said sample plate and said migration reservoir for bringing either one of these into contact with said capillary column ends, wherein said base plate is of such a throwaway type that said bottom portions of said wells are set at a thickness allowing formation of through holes with metal projections, said sample plate further comprising:

an electrode plate having a flat surface and having projections provided on said flat surface of said electrode plate in positions corresponding to said wells of said base plate for serving as said electrodes and having said connector part, and a fixing member fixing said electrode plate and said base plate to each other while inserting said projections of said electrode plate into said wells from said rear side of said base plate.

\* \* \* \* \*